US012236584B2

(12) United States Patent
Smith et al.

(10) Patent No.: US 12,236,584 B2
(45) Date of Patent: Feb. 25, 2025

(54) SYSTEMS AND METHODS FOR FACILITATING OPPORTUNISTIC SCREENING FOR CARDIOMEGALY

(71) Applicants: AI METRICS, LLC, Hoover, AL (US); THE UAB RESEARCH FOUNDATION, Birmingham, AL (US)

(72) Inventors: Andrew Dennis Smith, Hoover, AL (US); Robert B. Jacobus, Jr., Mountain Brook, AL (US); Paige Elaine Severino, Birmingham, AL (US)

(73) Assignees: AI METRICS, LLC, Hoover, AL (US); THE UAB RESEARCH FOUNDATION, Birmingham, AL (US)

( * ) Notice: Subject to any disclaimer, the term of this patent is extended or adjusted under 35 U.S.C. 154(b) by 551 days.

(21) Appl. No.: 17/544,491

(22) Filed: Dec. 7, 2021

(65) Prior Publication Data
US 2022/0180513 A1    Jun. 9, 2022

Related U.S. Application Data

(60) Provisional application No. 63/122,390, filed on Dec. 7, 2020.

(51) Int. Cl.
G06T 7/00 (2017.01)
G06T 7/62 (2017.01)
(Continued)

(52) U.S. Cl.
CPC ............ *G06T 7/0012* (2013.01); *G06T 7/62* (2017.01); *G16H 30/40* (2018.01); *G16H 50/30* (2018.01);
(Continued)

(58) Field of Classification Search
CPC ........ G16H 50/30; G16H 50/20; G16H 20/00; G16H 30/40; G06T 2207/10081;
(Continued)

(56) References Cited

U.S. PATENT DOCUMENTS

2020/0151871 A1* 5/2020 Putha .................. G06F 40/30

FOREIGN PATENT DOCUMENTS

WO    WO-2016138522 A1 *  9/2016

OTHER PUBLICATIONS

Bruns, S., Wolterink, J. M., Takx, R. A., van Hamersvelt, R. W., Suchá, D., Viergever, M. A., . . . & Išgum, I. (2020). Deep learning from dual-energy information for whole-heart segmentation in dual-energy and single-energy non-contrast-enhanced cardiac CT. Medical physics, 47(10), 5048-5060. (Year: 2020).*

(Continued)

*Primary Examiner* — Andrae S Allison
*Assistant Examiner* — Emmanuel Silva-Avina
(74) *Attorney, Agent, or Firm* — Workman Nydegger

(57) ABSTRACT

A computer-implemented method for facilitating opportunistic screening for cardiomegaly includes obtaining a set of computed tomography (CT) images. The set of CT images captures at least a portion of a heart of a patient, and the set of CT images is captured for a purpose independent of assessing cardiomegaly. The method further includes using the set of CT images as an input to an artificial intelligence (AI) module configured to determine a heart measurement based on CT image set input. The method also includes obtaining heart measurement output generated by the AI module and, based on the heart measurement output, classifying the patient into one of a plurality of risk levels for cardiomegaly. The classification is operable to trigger additional action based on the corresponding risk level for the patient.

16 Claims, 14 Drawing Sheets

(51) Int. Cl.
  *G16H 30/40* (2018.01)
  *G16H 50/30* (2018.01)
(52) U.S. Cl.
  CPC ............... *G06T 2207/10081* (2013.01); *G06T 2207/20081* (2013.01); *G06T 2207/30048* (2013.01)
(58) Field of Classification Search
  CPC . G06T 2207/20081; G06T 2207/30048; G06T 7/0012; G06T 7/62; G06T 2211/40; G06T 2211/441
  USPC ......................................................... 382/131
  See application file for complete search history.

(56) References Cited

OTHER PUBLICATIONS

Draelos, R. L., Dov, D., Mazurowski, M. A., Lo, J. Y., Henao, R., Rubin, G. D., & Carin, L. (2020). Machine-Learning-Based Multiple Abnormality Prediction with Large-Scale Chest Computed Tomography Volumes. arXiv preprint arXiv:2002.04752. (Year: 2020).*

Moreta-Martínez, Rafael, et al. "Multi-cavity heart segmentation in non-contrast non-ECG gated CT scans with F-CNN." International Workshop on Thoracic Image Analysis. Cham: Springer International Publishing, 2020. (Year: 2020).*

* cited by examiner

800

802 → Patient: Jane Doe   804 → MRN#: 123457   806 → Age: 67   808 → Gender: F

Imaging Exam: CT abdomen and Pelvis w contrast ← 810

Clinical Information: Status post fall ← 812

Whole Heart

814

Left Ventricle

816

Inner Chest

820

Outer Chest

822

| Structure 818 | Measurement 826 | Normal Range 828 | Percentile |
|---|---|---|---|
| Whole Heart: | 134 cm² | 84-120 cm² | 97th |
| Left Ventricle: | 30 cm² | 24-38 cm² | 65th |
| Inner Chest: | 363 cm² | 295-418 cm² | |
| Outer Chest: | 582 cm² | 357-671 cm² | 830 |

824

SYSTEMS AND METHODS FOR FACILITATING OPPORTUNISTIC SCREENING FOR CARDIOMEGALY

CROSS-REFERENCE TO RELATED APPLICATIONS

This application claims priority to U.S. Provisional Patent Application Ser. No. 63/122,390, filed Dec. 7, 2021, and titled "SYSTEMS AND METHODS FOR FACILITATING OPPORTUNISTIC SCREENING FOR CARDIOMEGALY", the entirety of which is incorporated herein by this reference.

BACKGROUND

Cardiomegaly refers to enlargement of the heart and/or portions thereof, such as enlargement of the right ventricle, the left ventricle, the right atrium, and/or the left atrium. Cardiomegaly may occur as a result of various pathologic processes, such as, for example, coronary artery disease, hypertensive heart disease, valvular heart disease, pulmonary diseases, infectious myocarditis, infiltrative/deposition disease, toxin-induced cardiomyopathy, autoimmune cardiomyopathy, and arrhythmia. It may also be the result of genetic predispositions such as in congenital heart disorders or familial cardiomyopathy, but in some instances, it is idiopathic. Cardiomegaly can be serious and is associated congestive heart failure and with a higher risk of sudden cardiac death.

Cardiomegaly can be caused by heart chamber dilatation or hypertrophy. Dilated cardiomyopathy is characterized by dilatation of the right ventricle, the left ventricle, the right atrium, and/or the left atrium. Hypertrophic cardiomyopathy is caused by hypertrophy, or thickening, of the wall of the left ventricular hypertrophy.

Cardiomegaly is primarily diagnosed through narrowly tailored imaging techniques, and for a significant number of patients, cardiomegaly leads to death within years of diagnosis. For example, a transthoracic echocardiogram may be used to assess ventricle and atrial size and systolic/diastolic function. Similarly, cardiac magnetic resonance imaging (MRI) or cardiac gated computed tomography (CT) may be used to evaluate ventricle mass, size, and/or function. A chest X-ray may be generally suggestive of cardiomegaly but fails to amount to a robust diagnostic tool vis-à-vis cardiomegaly.

Many patients having cardiomegaly are asymptomatic, and the presence of symptoms alone is neither sensitive nor specific to a diagnosis of cardiomegaly. Consequently, few instances of cardiomegaly are diagnosed as a result of the patient seeking medical attention for that purpose. Furthermore, many symptomatic patients do not immediately undergo conventional specialized imaging techniques to diagnose cardiomegaly. For example, symptoms associated with cardiomegaly may include shortness of breath, peripheral edema, abdominal distension, fatigue, poor exercise tolerance, palpitations, lightheadedness, syncope, angina, anorexia, nausea, or early satiety. These symptoms are associated with myriad other ailments, and physicians may initially perform diagnostic tests that are not narrowly tailored for diagnosing cardiomegaly. This can lead to unnecessary or wasteful expenditures of healthcare resources and additional time before the patient can be properly treated.

Accordingly, there are a number of disadvantages with current methods for screening for cardiomegaly that may be addressed.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

Embodiments of the present disclosure are directed to systems and methods for facilitating opportunistic screening for cardiomegaly.

In one aspect, a computer-implemented method for facilitating opportunistic screening for cardiomegaly includes obtaining a set of computed tomography (CT) images. The set of CT images captures at least a portion of a heart of a patient, and the set of CT images is captured for a purpose independent of assessing cardiomegaly. The method further includes using the set of CT images as an input to an artificial intelligence (AI) module configured to determine a heart measurement based on CT image set input. The method also includes obtaining heart measurement output generated by the AI module and, based on the heart measurement output, classifying the patient into one of a plurality of risk levels for cardiomegaly. The classification is operable to trigger additional action based on the corresponding risk level for the patient.

In another aspect, a computer-implemented method for facilitating opportunistic screening for cardiomegaly includes obtaining a CT imaging dataset, where the CT imaging dataset includes a plurality of sets of CT images, and where each set of CT images of the plurality of sets of CT images is associated with a respective patient of a plurality of patients. The method also includes determining a set of heart measurements comprising one or more separate heart measurements for each set of CT images of the plurality of sets of CT images. The set of heart measurements is determined using an artificial intelligence (AI) module configured to determine heart measurement output based on CT image set input. The method further includes, based on the set of heart measurements, classifying a subset of patients of the plurality of patients into one or more risk levels for cardiomegaly. The method also includes accessing medical record information associated with the subset of patients, and determining, based on the medical record information, one or more patients of the subset of patients that lack corresponding medical record information related to cardiomegaly. The method furthermore includes providing a notification to one or more entities associated with the one or more patients.

In another aspect, a computer-implemented method for facilitating population health research using CT imaging datasets includes obtaining a CT imaging dataset for a population, where the CT imaging dataset includes a plurality of sets of CT images, and where each set of CT images of the plurality of sets of CT images is associated with a respective person. The method further includes determining a set of heart measurements comprising one or more separate heart measurements for each set of CT images of the plurality of sets of CT images. The set of heart measurements is determined using an artificial intelligence (AI) module configured to determine heart measurement output based on CT image set input. The method also includes obtaining patient outcome data comprising one or more patient outcomes for each respective person associated with a set of CT images and determining one or more correlations between the set of heart measurements and the patient outcome data.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope.

The disclosure will be described and explained with additional specificity and detail through the use of the accompanying drawings in which.

DETAILED DESCRIPTION

Figure 1:
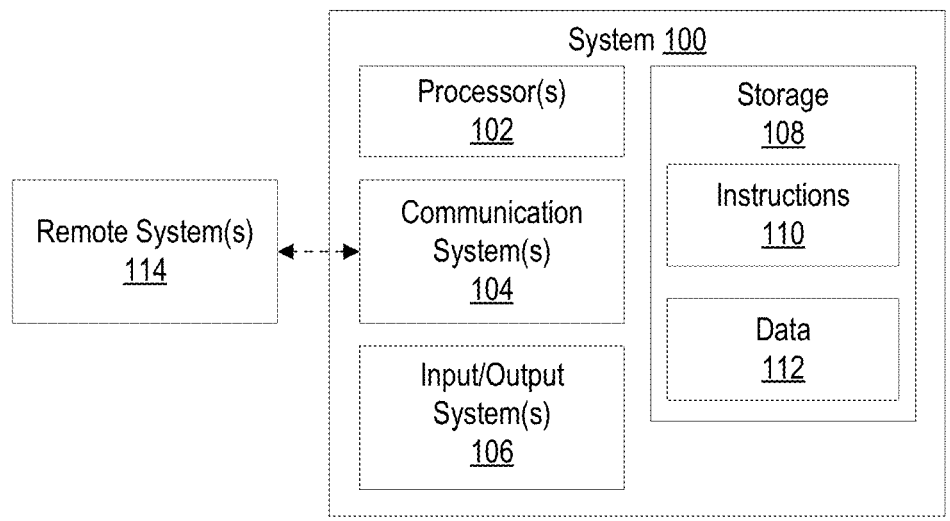
FIG. 1 illustrates an example computer system that may comprise or implement one or more embodiments of the present disclosure.

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, any headings used herein are for organizational purposes only, and the terminology used herein is for the purpose of describing the embodiments. Neither are not meant to be used to limit the scope of the description or the claims.

Embodiments of the present disclosure are directed to systems and methods for facilitating opportunistic screening for cardiomegaly, as well as systems and methods for facilitating population health research using CT imaging datasets.

As used herein, the term "physician" generally refers to a medical doctor, or a specialized medical doctor, such as a radiologist, primary care physician, cardiologist, or other medical doctor. This term may, when contextually appropriate, include any other medical professional, including any licensed medical professional or other healthcare provider, such as a physician's assistant, a nurse, a veterinarian (such as, for example, when the patient is a non-human animal), etc.

The term "patient" generally refers to any animal, for example a mammal, under the care of a physician, as that term is defined herein, with typical reference to humans who have undergone CT imaging for, typically, a non-cardiomegaly-related purpose. Such humans may include research participants, individuals under the care of a medical professional, and/or others. For the purpose of the present application, a "patient" may be interchangeable with an "individual" or "person." In some embodiments, the individual is a human patient.

Overview of Disclosed Embodiments

In some embodiments, a computer-implemented method for facilitating opportunistic screening for cardiomegaly includes obtaining a set of computed tomography (CT) images. The set of CT images captures at least a portion of a heart of a patient, and the set of CT images is captured for a purpose independent of assessing cardiomegaly. The method further includes using the set of CT images as an input to an artificial intelligence (AI) module configured to determine a heart measurement based on CT image set input. The method also includes obtaining heart measurement output generated using the AI module and, based on the heart measurement output, classifying the patient into one of a plurality of risk levels for cardiomegaly. The classification is operable to trigger additional action based on the corresponding risk level for the patient.

In some embodiments, a computer-implemented method for facilitating opportunistic screening for cardiomegaly includes obtaining a CT imaging dataset, where the CT imaging dataset includes a plurality of sets of CT images, and where each set of CT images of the plurality of sets of CT images is associated with a respective patient of a plurality of patients. The method also includes determining a set of heart measurements comprising one or more separate heart measurements for each set of CT images of the plurality of sets of CT images. The set of heart measurements is determined using an artificial intelligence (AI) module configured to determine heart measurement output based on CT image set input. The method further includes, based on the set of heart measurements, classifying a subset of patients of the plurality of patients into one or more risk levels for cardiomegaly. The method also includes accessing medical record information associated with the subset of patients, and determining, based on the medical record information, one or more patients of the subset of patients that lack corresponding medical record information related to cardiomegaly and/or other cardiac diseases (e.g., arrhythmia). The method furthermore includes providing a notification to one or more entities associated with the one or more patients.

In some embodiments, a computer-implemented method for facilitating population health research using CT imaging datasets includes obtaining a CT imaging dataset for a population, where the CT imaging dataset includes a plurality of sets of CT images, and where each set of CT images of the plurality of sets of CT images is associated with a respective person. The method further includes determining a set of heart measurements comprising one or more separate heart measurements for each set of CT images of the plurality of sets of CT images. The set of heart measurements is determined using an artificial intelligence (AI) module configured to determine heart measurement output based on CT image set input. The method also includes obtaining research participant outcome data comprising one or more patient outcomes for each respective person associated with a set of CT images and determining one or more associations between the set of heart measurements and the research participant outcome data. Research participant outcome data could include current and/or future cardiovascular conditions or events, current and/or future cardiovascular interventions, survival, laboratory data, genomic data, proteomic data, etc.

Those skilled in the art will appreciate, in view of the present disclosure, that at least some of the disclosed embodiments may address deficiencies associated with detection of cardiomegaly. For example, at least some embodiments of the present disclosure utilize routine CT images to screen for cardiomegaly in an opportunistic manner. Routine computed tomography (CT) images are captured for patients for a broad variety of purposes, such as to detect or evaluate cancer, tumors, emphysema, liver masses, internal bleeding and/or infections, bone and/or joint problems, causes of internal pain, as well as myriad other purposes, including many symptoms associated with cardiomegaly described hereinabove. Thus, routine CT images may be captured and available for patients in many instances where medical images narrowly tailored to detecting cardiomegaly (e.g., echocardiogram, cardiac MM, or gated CT) are not captured or are not yet captured.

Routine CT images may be captured of a predefined portion of a patient's body or of a patient's entire body. For example, physicians may capture a set of chest CT images, a set of abdomen CT images, a set of chest and abdomen CT images, a set of abdomen and pelvis CT images, etc. As used herein, "routine" CT images refer to CT images captured under general and conventional CT imaging conditions without any specific constraints applied to specifically configure the CT images for the assessment of cardiomegaly. For example, "routine" CT images are captured without leads positioned on the patient for performing cardiac gated CT imaging to capture a particular cycle of the patient's heart. Thus, "routine" CT images omit any type of cardiac gated CT images/imaging and are distinct from medical images narrowly tailored for detecting cardiomegaly. Routine CT images may comprise non-contrast CT images, contrast-enhanced CT images, high-resolution CT images, low radiation dose CT images for any purpose (including but not limited to lung cancer screening or colonography) and/or other CT images in accordance with the above definition.

Accordingly, opportunistic screening for cardiomegaly using routine CT images, as described herein, may facilitate detection of cardiomegaly in instances where narrowly tailored imaging techniques for detecting cardiomegaly would not be initially utilized by medical practitioners. For example, a physician may perform a routine chest or abdomen CT scan (rather than a scan specifically tailored to detecting cardiomegaly) for a non-cardiomegaly-related purpose. The routine CT images may automatically be used to classify the patient into a risk level for cardiomegaly, even where the patient did not seek treatment for cardiomegaly or where the physician did not order the CT scan for the explicit purpose of detecting cardiomegaly. Thus, at least some embodiments of the present disclosure may facilitate earlier detection of cardiomegaly, which can beneficially increase patient care and potentially prevent unexpected or even catastrophic events stemming from undiagnosed cardiomegaly.

Opportunistic screening for cardiomegaly, as described herein, may be performed at the individual patient level or at a population level. For example, at regular or irregular intervals, a hospital or other medical facility/clinic may use captured sets of routine CT scans for patients as input to an AI module to screen the patients for cardiomegaly. The output of the AI module may facilitate classifying certain patients as appearing to be experiencing cardiomegaly. Medical record information (and/or other information) may be evaluated to determine whether the patients that appear to be experiencing cardiomegaly have not been diagnosed as experiencing cardiomegaly or related conditions. Relevant entities associated with such patients that appear to be experiencing cardiomegaly but have not been diagnosed may then be notified (e.g., through an online patient portal, via their primary care physician or specialist, etc.). Thus, at least some embodiments of the present disclosure may advantageously detect cardiomegaly that might otherwise have gone undetected to the detriment of patients.

Furthermore, at least some embodiments of the present disclosure may operate on CT imaging datasets of populations to explore relationships between heart measurements obtained from routine CT images and patient outcomes for different populations.

Exemplary Systems and Methods for Facilitating Opportunistic Screening of Cardiomegaly Having described some of the various high-level features and benefits of the disclosed embodiments, attention will now be directed to FIGS. 1 through 8. These Figures illustrate various conceptual representations, architectures, methods, and/or supporting illustrations related to the disclosed embodiments.

FIG. 1 illustrates an example computer system 100 that may comprise or implement one or more embodiments of the present disclosure. As is illustrated in FIG. 1, the computer system 100 includes processor(s) 102, communication system(s) 104, I/O system(s) 106, and storage 108. Although FIG. 1 illustrates the computer system 100 as including particular components, it will be appreciated, in view of the present disclosure, that a computer system 100 may comprise any number of additional or alternative components.

The processor(s) 102 may comprise one or more sets of electronic circuitry that include any number of logic units, registers, and/or control units to facilitate the execution of computer-readable instructions (e.g., instructions that form a computer program). Such computer-readable instructions may be stored within storage 108. The storage 108 may comprise physical system memory and may be volatile, non-volatile, or some combination thereof. Furthermore, storage 108 may comprise local storage, remote storage, or some combination thereof. Additional details related to processors (e.g., processor(s) 102) and computer storage media (e.g., storage 108) will be provided hereinafter.

As used herein, processor(s) 102 may comprise or be configurable to execute any combination of software and/or hardware components that are operable to facilitate processing using machine learning models or other artificial intelligence-based structures/architectures. For example, processor(s) 102 may comprise and/or utilize hardware components or computer-executable instructions operable to carry out function blocks and/or processing layers configured in the form of, by way of non-limiting example, single-layer neural networks, feed forward neural networks, radial basis function networks, deep feed-forward networks, recurrent neural networks, long-short term memory (LSTM) networks, gated recurrent units, autoencoder neural networks, variational autoencoders, denoising autoencoders, sparse autoencoders, Markov chains, Hopfield neural networks, Boltzmann machine networks, restricted Boltzmann machine networks, deep belief networks, deep convolutional networks (or convolutional neural networks), deconvolutional neural networks, deep convolutional inverse graphics networks, generative adversarial networks, liquid state machines, extreme learning machines, echo state networks, deep residual networks, Kohonen networks, support vector machines, neural Turing machines, and/or others.

As will be described in more detail, the processor(s) 102 may be configured to execute instructions 110 stored within storage 108 to perform certain actions associated with facilitating opportunistic screening for cardiomegaly. The actions may rely at least in part on data 112 stored on storage 108 in a volatile or non-volatile manner (e.g., one or more sets of routine CT images). In some instances, the actions may rely at least in part on communication system(s) 104 for receiving data from remote system(s) 114, which may include, for example, other computer systems or computing devices, medical imaging devices/systems, and/or others.

The communications system(s) 104 may comprise any combination of software or hardware components that are operable to facilitate communication between on-system components/devices and/or with off-system components/devices. For example, the communications system(s) 104 may comprise ports, buses, or other physical connection apparatuses for communicating with other devices/components (e.g., USB port, SD card reader, and/or other apparatus). Additionally, or alternatively, the communications system(s) 104 may comprise systems/components operable to communicate wirelessly with external systems and/or devices through any suitable communication channel(s), such as, by way of non-limiting example, Bluetooth, ultra-wideband, WLAN, infrared communication, and/or others.

Furthermore, in some instances, the actions that are executable by the processor(s) 102 may rely at least in part on I/O system(s) 106 for receiving user input from one or more users. I/O system(s) 106 may include any type of input or output device such as, by way of non-limiting example, a touch screen, a display, a mouse, a keyboard, a controller, and/or others, without limitation.

Figure 2:
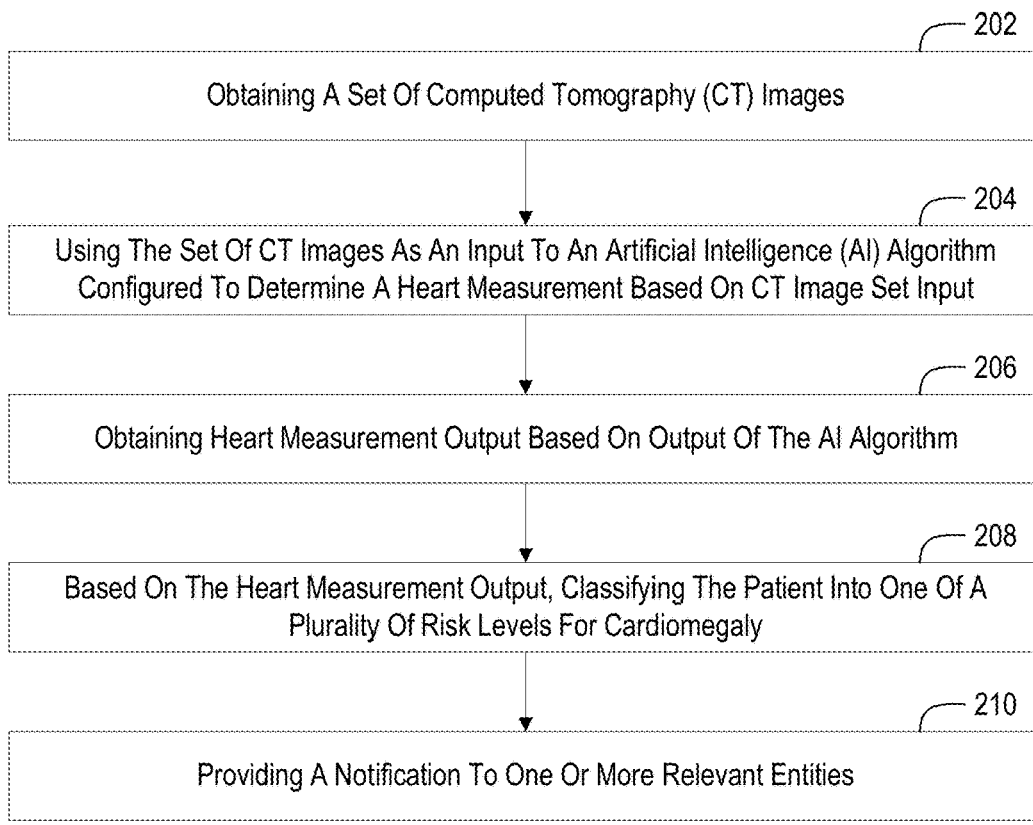
FIGS. 2 and 3 illustrate example flow diagrams depicting acts associated with facilitating opportunistic screening for cardiomegaly.
Figure 3:
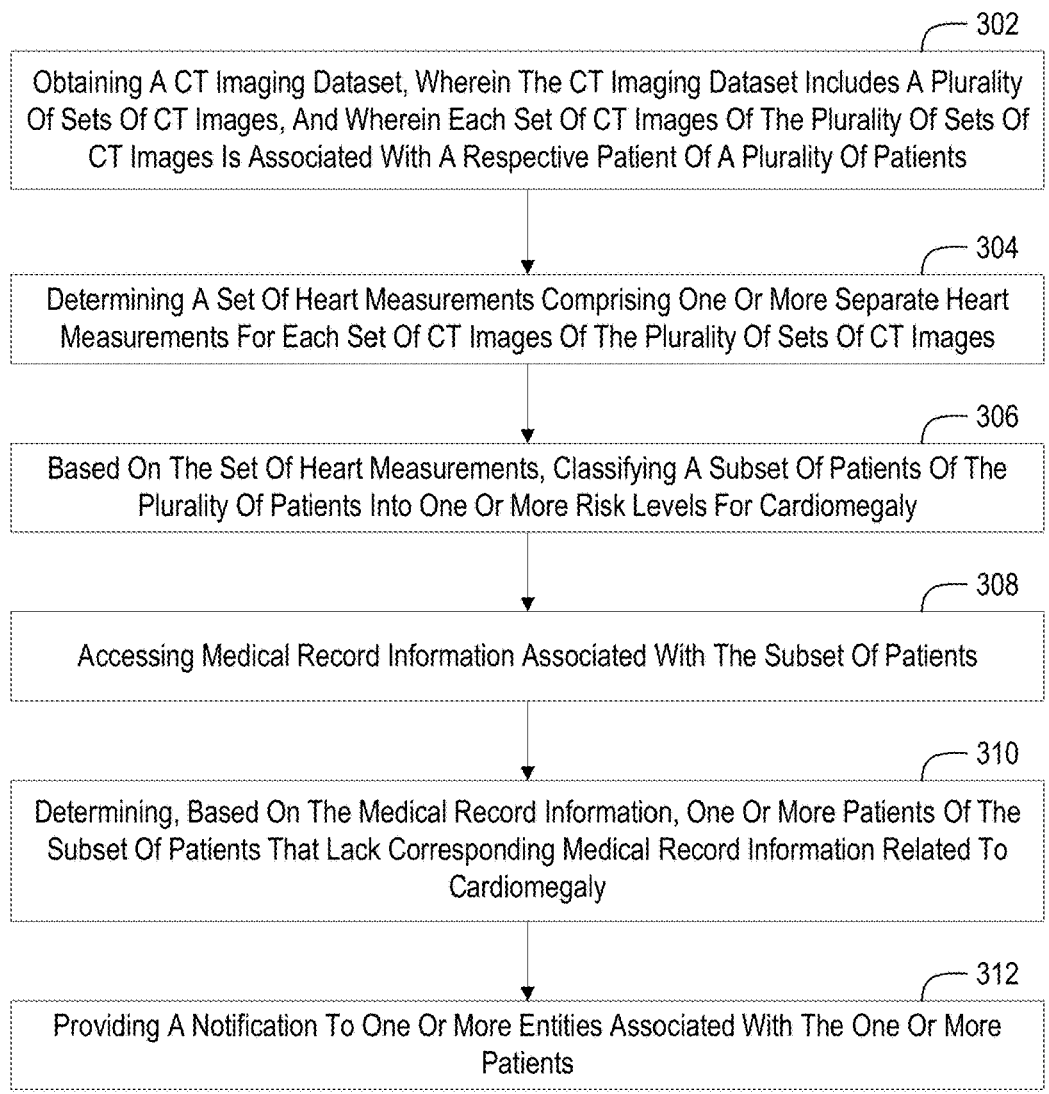

Some embodiments of the present disclosure can also be described in terms of acts (e.g., acts of a method) for accomplishing a particular result. Along these lines, FIGS. 2 and 3 illustrate example flow diagrams 200 and 300, respectively, depicting acts associated with facilitating opportunistic screening for cardiomegaly. Although the acts shown in flow diagrams 200 and 300 (and/or others) may be illustrated and/or discussed in a certain order, no particular ordering is required unless specifically stated or required because an act is dependent on another act being completed prior to the act being performed. Furthermore, it should be noted that not all acts represented in flow diagrams 200 and 300 are essential for facilitating opportunistic screening for cardiomegaly.

In some instances, the various acts disclosed herein are performed using a computer system 100. For instance, code for configuring the computer system 100 to perform the various acts disclosed herein may be stored as instructions 110 on storage 108, and such instructions 110 may be executable by the processor(s) 102 (and/or other components) to facilitate carrying out of the various acts.

Act 202 of flow diagram 200 includes obtaining a set of computed tomography (CT) images. The set of CT images may comprise contrast-enhanced, non-contrast, high resolution, and/or any other format of CT images. The set of CT images comprises routine CT images as described hereinabove. In this regard, the set of CT images may be captured in a non-gated manner and for a purpose that is independent of assessing cardiomegaly. Accordingly, the set of CT images is distinct from cardiac gated CT image sets.

The set of CT images captures at least a portion of a heart of a patient whose body is represented in the set of CT images. For instance, the set of CT images may be a routine set of chest CT images or a routine set of abdominal CT images. In some instances, although a routine set of abdominal CT images may not provide a representation of the entire heart of a patient, a routine set of abdominal CT images may capture the largest portions of the patient's heart. Accordingly, a routine set of abdominal CT images may include one or more cross-sectional images that provide a largest possible cross-sectional representation of one or more portions of the patient's heart (e.g., the total heart as a unit, the left ventricle, the right ventricle, the left atrium, the right atrium, etc.).

Act 204 of flow diagram 200 includes using the set of CT images as an input to an artificial intelligence (AI) module configured to determine a heart measurement based on CT image set input. One will appreciate, in view of the present disclosure, that the AI module may take on any suitable form for determining heart measurement output based on CT image set input.

In some embodiments, the AI module comprises one or more machine learning modules that is/are configured/trained to identify a subset of CT images from CT image set input. The subset of CT images includes one or more CT images that provide a largest representation of one or more portions of a heart represented in the CT image set input (e.g., the heart of the patient associated with the set of CT images described with reference to act 202). Accordingly, the subset of CT images may provide a basis for determining a largest measurement associated with one or more portions of the heart represented in the CT image set input. The AI module(s) may be trained on a training dataset including input data comprising CT image sets. The training dataset may further comprise ground truth output, which may comprise tags indicating which CT image(s) of each respective set of CT images provide(s) a largest representation of one or more portions or aspects of a heart. In some instances, the AI module(s) are configured to segment each of the CT images to identify whether a heart is represented in each of the CT images, and, where a heart is detected, the AI module(s) may be configured to determine automated heart measurements associated with the heart. The CT image(s) providing a largest representation of the one or more portions or aspects of the heart may thus be identified by comparing the automated heart measurements obtained by the AI module(s). Appropriate training data may be utilized to configure the AI module(s) for such purposes (e.g., CT image input and ground truth tags indicating whether a heart or heart structure is present in the CT image and/or indicating measurements for the heart or heart structure).

The AI module(s) may be configured to provide a size measurement of the entire heart and/or a portion/aspect thereof to facilitate assessing of cardiomegaly. For example, the AI module(s) may be trained/configured to measure the heart size on the axial slice showing the largest representation of the heart. The AI module(s) may provide heart size measurements that include the longest dimension of the heart (e.g., major axis) and/or a length of the heart that is orthogonal to the longest dimension (e.g., short axis or minor axis), and/or an average of the major and minor axis of the heart, and/or an area of the heart. Additionally, or alternatively, the AI module(s) may be directed to provide a volumetric measurement of the entire heart.

Figure 5A:
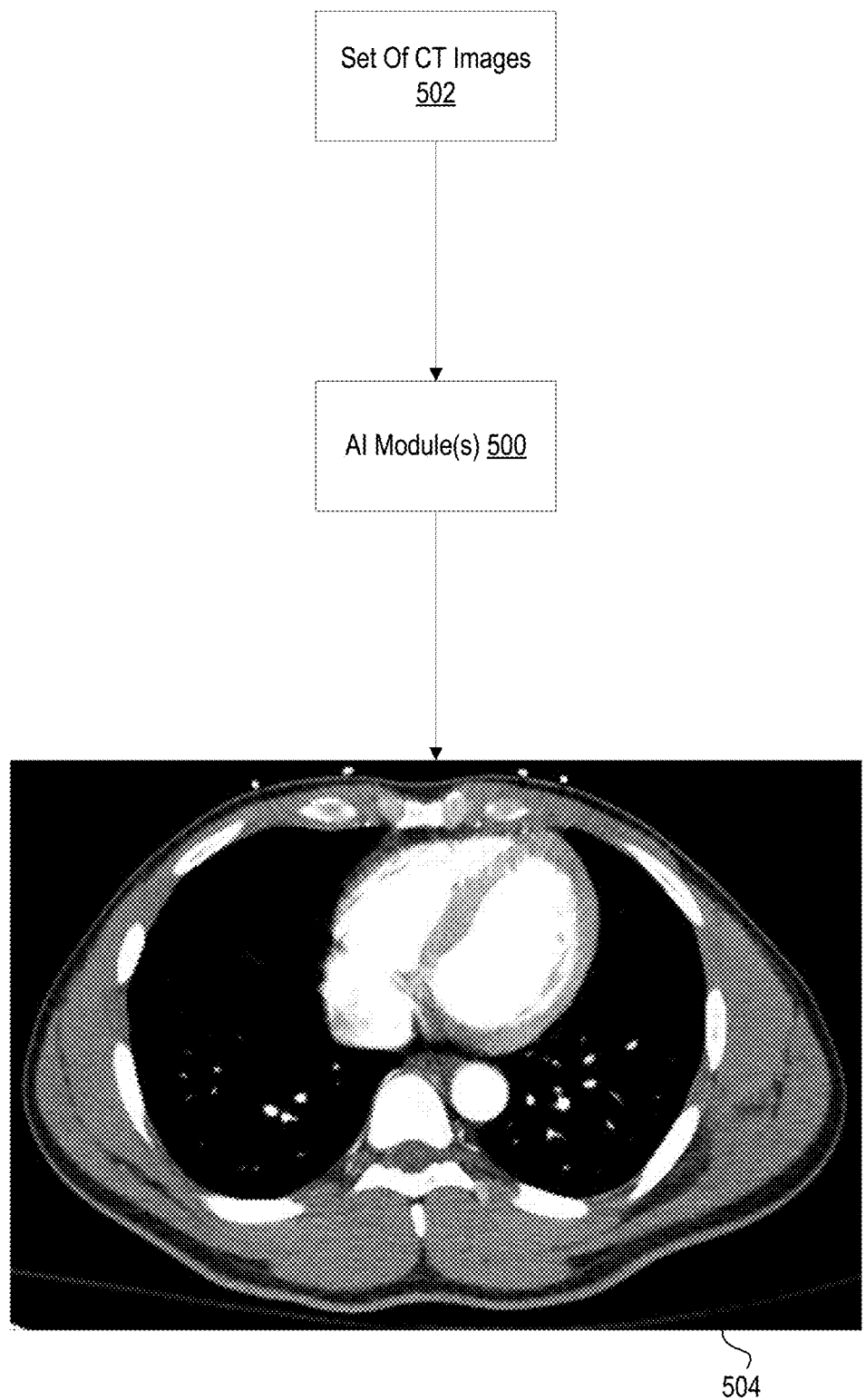
FIGS. 5A through 7C illustrate example CT images and heart measurements associated with opportunistic screening for cardiomegaly.

By way of illustration, attention is directed to FIG. 5A, which shows an example contrast-enhanced CT image 504 identified from a set of CT images 502 associated with a particular patient (e.g., an abdominal CT image set for a 46-year-old male, in the example shown in FIG. 5A). As noted above, the set of CT images 502 may comprise a routine set of CT images captured for a purpose independent of detecting cardiomegaly (e.g., the set of CT images 502 may be captured in a non-gated manner). For instance, the patient associated with the set of CT images 502 may have reported abdominal pain, which does not ordinarily trigger medical imaging focused on the detection of cardiomegaly (e.g., gated CT imaging). A patient's report of abdominal pain ordinarily triggers the capturing of a routine diagnostic set of CT images (non-gated CT images, set of CT images 502).

Figure 5B:
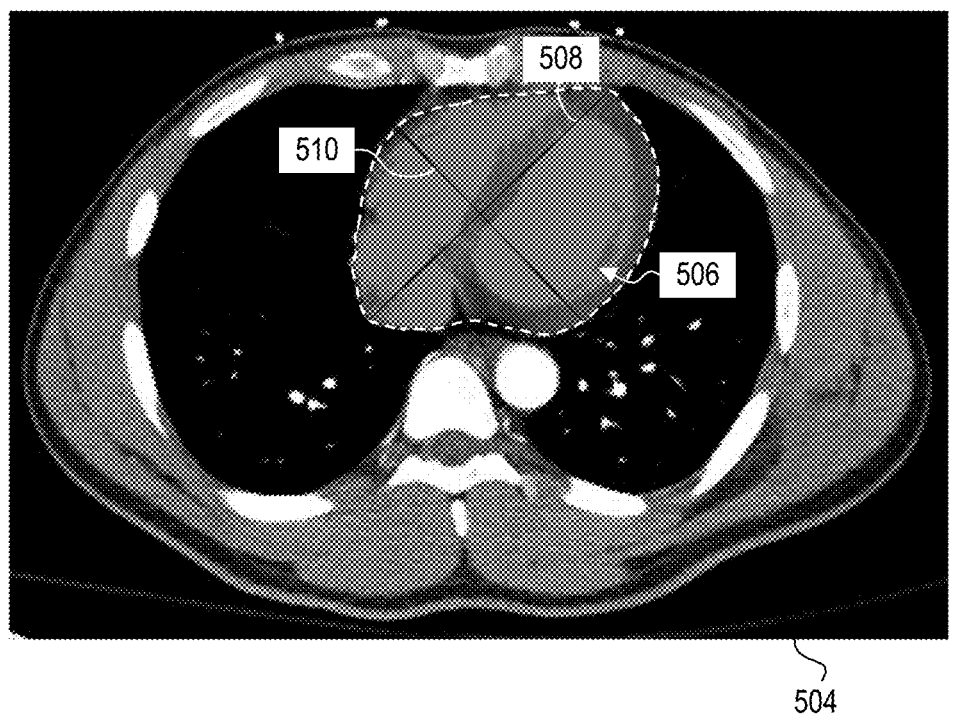

FIG. 5A illustrates the set of CT images 502 being provided as input to AI module(s) 500. The AI module(s) 500 are configured to identify one or more CT images of an input set of CT images that provides a largest measurement associated with a patient's heart represented in the input set of CT images. FIG. 5A illustrates a CT image 504, which may be identified utilizing the AI module(s) 500 as depicting a largest representation of a whole heart (and/or structure within the heart) of a patient. FIG. 5B illustrates the example CT image from FIG. 5A with an overlay illustrating an identification of an area 506 of the patient's whole heart (bounded by a white dashed line), a major axis 508 associated with the patient's whole heart, and a minor axis 510 associated with the patient's whole heart. As discussed above, such measurements may be obtained automatically utilizing the AI module(s) (e.g., AI module(s) 500 of FIG. 5A).

In some embodiments, the AI module(s) may be directed to measure one or more cardiac chambers, including the left ventricle, right ventricle, left atrium, and/or right atrium. The AI module(s) may be directed to measure one or more chambers of the heart on one axial slice or on multiple axial slices, whereby the AI module(s) may be directed to one or more slices where each chamber of the heart is the largest in size. The AI module(s) may provide size measurements of each chamber that include the longest dimension of the chamber (e.g., major axis) and/or a length of the chamber that is orthogonal to the longest dimension (e.g., short axis or minor axis), and/or an average of the major and minor axis of the chamber, and/or an area of the chamber. Additionally, or alternatively, the AI module(s) may be directed to provide a volumetric measurement of one or more chambers of the heart.

Figure 5C:
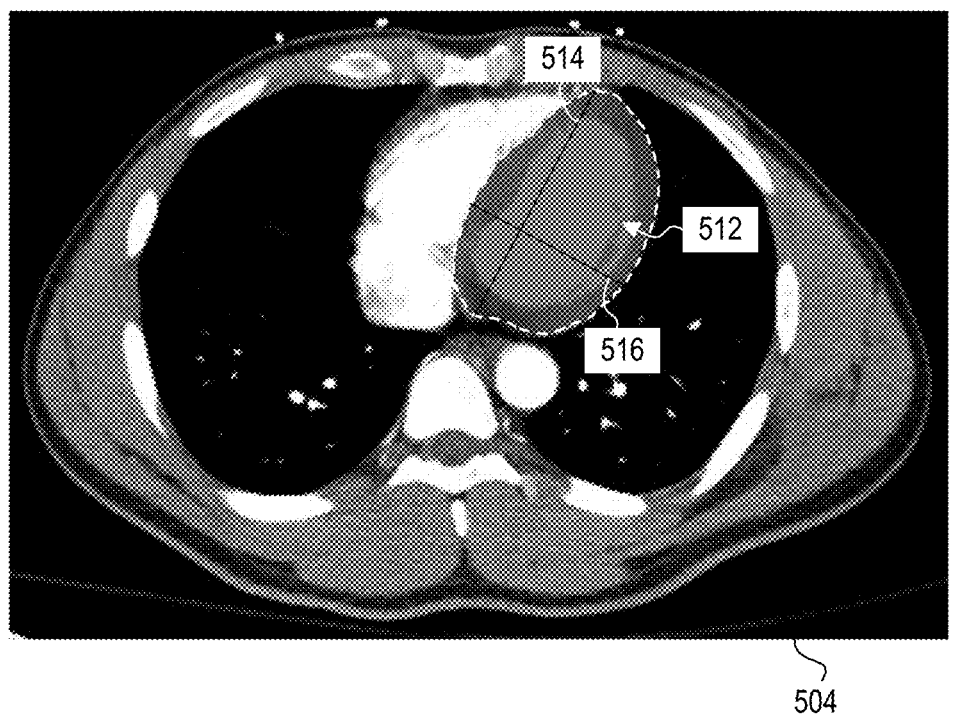

By way of illustration, attention is directed to FIG. 5C, which shows the CT image 504 of FIGS. 5A and 5B, but with an overlay illustrating an identification of an area 512 of the left ventricle of the patient's heart, a major axis 514 associated with the left ventricle of the patient's heart, and a minor axis 516 associated with the left ventricle of the patient's heart. As discussed above, such measurements may be obtained automatically utilizing the AI module(s) (e.g., AI module(s) 500 of FIG. 5A).

One will appreciate, in view of the present disclosure, that although the whole heart measurements (FIG. 5B) and the left ventricular measurements (FIG. 5C) are illustrates as being measured from the same CT image, different measurements associated with a user's heart may be obtained using different CT images from the same set of CT images. For instance, one CT image may provide a largest representation of a user's whole heart, while a different CT image from the same set of CT images may provide a largest representation of the user's left ventricle.

Figure 6A:

As noted hereinabove, heart measurements may be obtained using various types of routine sets of CT images, aside from sets of abdominal sets of CT images as shown in FIGS. 5A through 5C. For example, FIG. 6A illustrates an example contrast-enhanced CT image 604 identified from a set of CT images 602 associated with a different patient (e.g., a chest CT image set for a 48-year-old male, in the example shown in FIG. 6A). The set of CT images 602 may comprise a routine set of CT images captured for a purpose independent of detecting cardiomegaly, such as to diagnose a cough reported by the patient (which does not ordinarily trigger medical imaging focused on the detection of cardiomegaly, such as gated CT imaging).

Figure 6B:
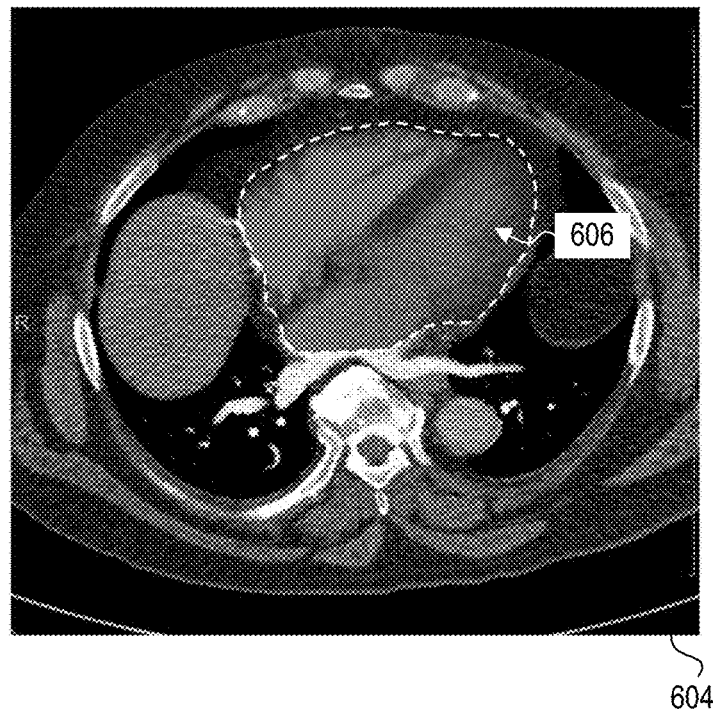

FIG. 6A illustrates the set of CT images 602 being provided as input to AI module(s) 600 (which may generally correspond to the AI module(s) 500). FIG. 6A illustrates a CT image 604, which may be identified utilizing the AI module(s) 600 as depicting a largest representation of a whole heart (and/or structure within the heart) of the patient. FIG. 6B illustrates the example CT image from FIG. 6A with an overlay illustrating an identification of an area 606 of the patient's whole heart. As discussed above, such measurements may be obtained automatically utilizing the AI module(s) (e.g., AI module(s) 600 of FIG. 6A).

Figure 6C:
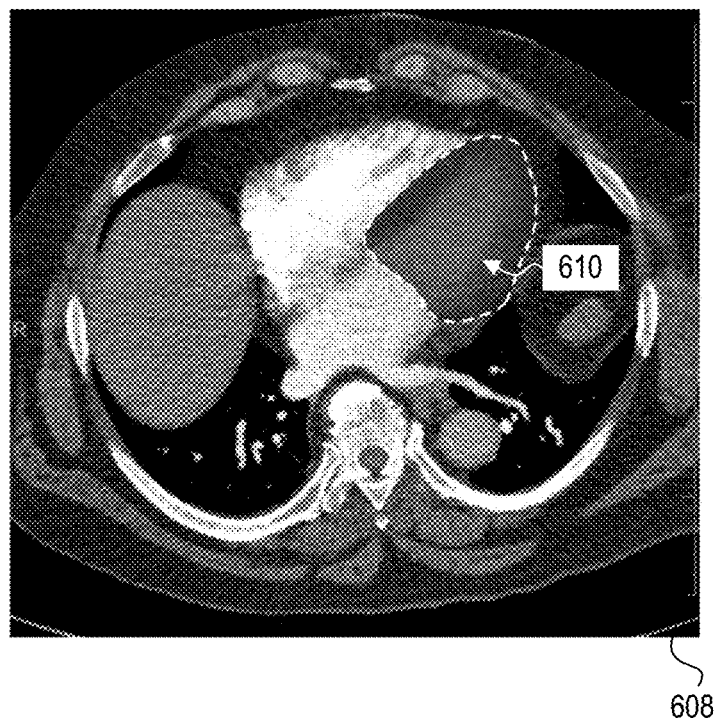

FIG. 6C shows a different CT image 608 from the set of CT images 602. The different CT image 608 may be identified by the AI module(s) 600 as providing a largest representation of a left ventricle of the patient. In FIG. 6C, the different CT image 608 includes an overlay illustrating an identification of an area 610 of the left ventricle of the patient's heart.

Figure 7A:
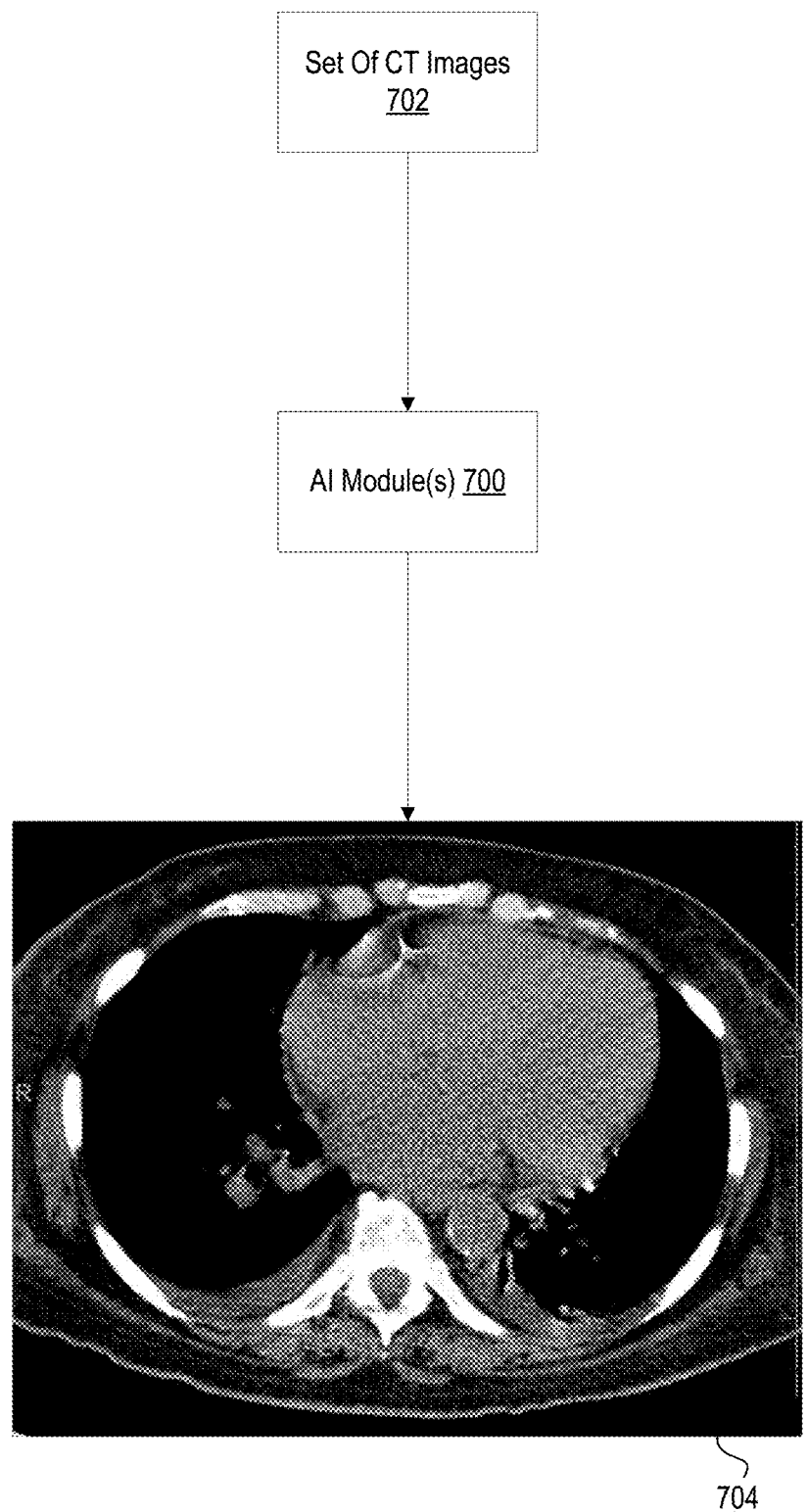

As another example, FIG. 7A illustrates an unenhanced CT image 704 identified utilizing AI module(s) 700 (which may correspond to AI module(s) 500) from a set of CT images 702 associated with a different patient (e.g., a chest CT image set for a 52-year-old female, in the example shown in FIG. 7A). The set of CT images 702 may comprise a routine set of CT images captured for a purpose independent of detecting cardiomegaly, such as to diagnose a cough reported by the patient.

Figure 7B:
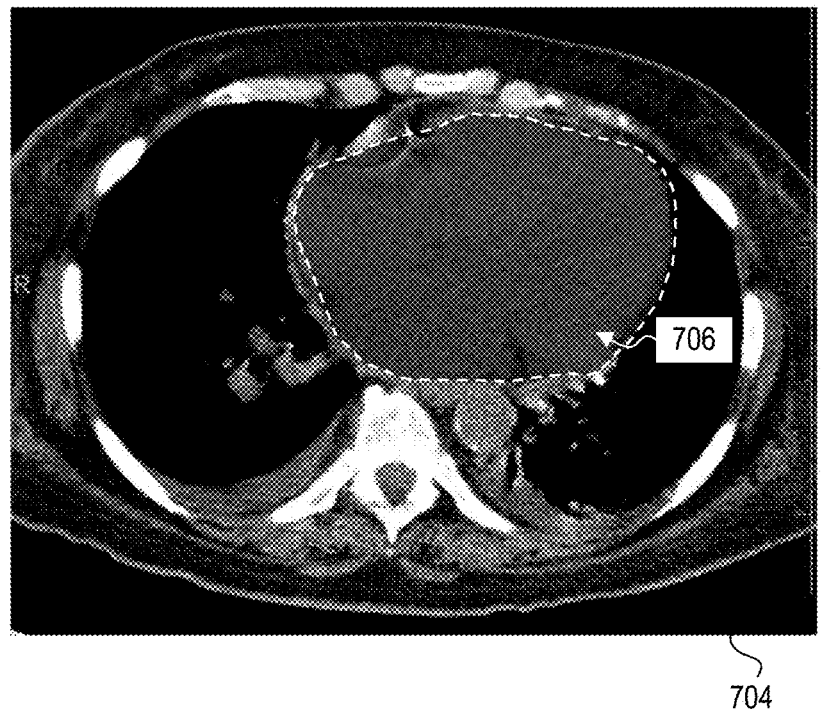

The CT image 704 may comprise a largest representation of a whole heart of the patient. FIG. 7B illustrates the example CT image from FIG. 7A with an overlay illustrating an identification of an area 706 of the patient's whole heart. As discussed above, such measurements may be obtained automatically utilizing the AI module(s) (e.g., AI module(s) 700 of FIG. 7A).

Figure 7C:
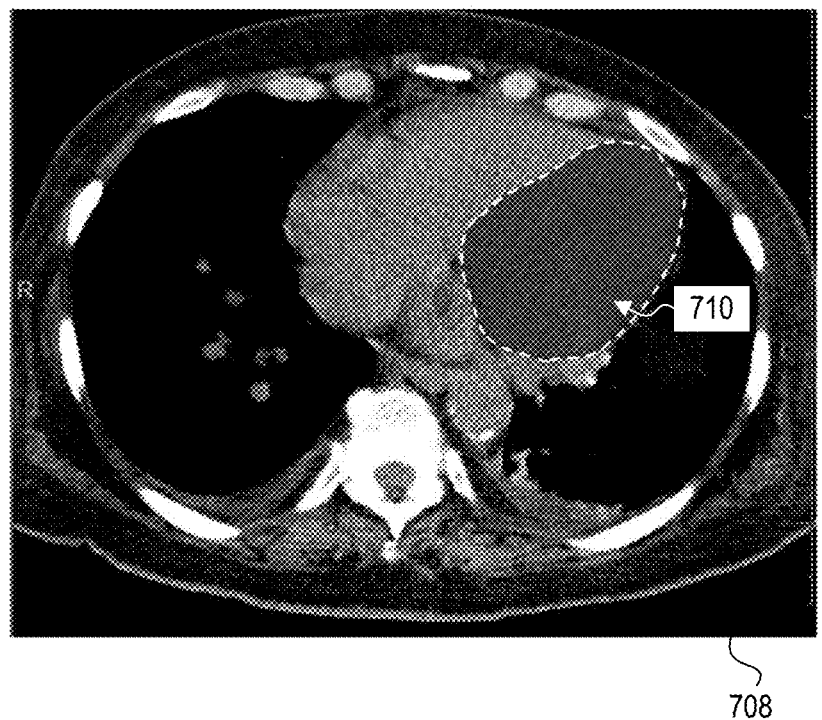

FIG. 7C shows a different CT image 708 from the set of CT images 702. The different CT image 708 may be identified by the AI module(s) 700 as providing a largest representation of a left ventricle of the patient. In FIG. 7C, the different CT image 708 includes an overlay illustrating an identification of an area 710 of the left ventricle of the patient's heart.

In some embodiments, the AI module(s) may be configured to measure the outer margins of the left ventricle, including the free wall, apex and inter-ventricular septum. In addition, or in the alternative, the AI module(s) may be configured to measure the inner chamber of the left ventricle, either including or excluding the papillary muscles. The AI module(s) (and/or additional module(s) for processing output of the AI module(s)) may be configured to calculate the left ventricular muscular mass and/or wall thickness by mathematically subtracting the inner chamber from the outer margins of the left ventricle. Furthermore, in some implementations, the AI module(s) may be directed to directly measure the left ventricular mass or to directly measure the thickness of the left ventricular wall, including the free wall, apex, and/or inter-ventricular septum.

Although referred to in the singular in act 204 (and in other portions of the present disclosure), an AI module may comprise one or more module components, such as separate AI modules that operate in series or in parallel with one another (e.g., one AI module for determining a largest whole heart slice and/or measurement, one AI module for determining a largest left ventricle slice and/or measurement, etc.).

In some embodiments, the heart size measurement may be adjusted and/or weighted for patient size, age, gender, race, and/or other factors. The AI module(s) may be configured to measure the size of the chest, such as the size of the inner chest (including the lungs and mediastinum) or the outer chest, including the chest wall, subcutaneous tissues and skin. For instance, the inner chest measurement may act as a surrogate for lean body mass, whereas the outer chest measurement may act as a surrogate for fat body mass. Thus, the AI module(s) may adjust and/or weight the heart size calculations to account for the size of the inner and/or outer chest (or may otherwise utilize the size of the inner and/or outer chest to classify patients' risk for cardiomegaly). In some instances, the AI module(s) may adjust and/or weight the heart size calculation using information from the DICOM header or electronic medical record including patient age, gender, height, body weight, body mass index, and/or body surface area.

In view of the foregoing, the AI module(s) may be configured to provide heart measurement output based on the largest measurement(s) of the portion(s) of the heart represented in the CT image set input. The largest measurement(s) may be associated with various structures of the heart represented in the CT image set input. For example, in some instances, the largest measurement(s) may measure ventricular wall thickness of the heart represented in the CT image set input. In some instances, the largest measurement(s) may comprise an axial length of the entire heart (e.g., as a single unit) represented in the CT image set input. An axial length may comprise a longest dimension of a structure (e.g., a major axis) and/or a length of the structure that is orthogonal to the longest dimension (e.g., a minor axis).

Additionally, or alternatively, the largest measurement(s) may measure an axial length of one or more chambers of the heart represented in the CT image set input, whether individually or combined. For example, the largest measurement(s) may provide a major and/or minor axis for the left ventricle, the right ventricle, the left atrium, the right atrium, or some combination thereof. Furthermore, in addition, or as an alternative, to axial length measurements, the largest measurement(s) may include area measurements of the left ventricle, the right ventricle, the left atrium, the right atrium, or some combination thereof (e.g., the total unitary area of the heart represented in the CT image set input).

Accordingly, the AI module(s) may be configured to output one or more largest measurements in various forms (e.g., area, length, thickness) and that may be representative of various heart structures (e.g., ventricular wall(s), the entire heart, the left ventricle, the right ventricle, the left atrium, the right atrium, and/or others). In some implementations, heart measurement output is generated utilizing one or more additional module(s) for processing output of the AI module(s). For example, the AI module(s) may be configured to measure the inner chamber and the outer margin of the left ventricle, while one or more separate modules are configured to subtract the outer margin measurement from the inner chamber measurement.

In some instances, different CT images within the CT image set input may provide largest measurements for different portions of the heart. For example, one CT image may provide a largest representation of the total area of the heart, whereas a separate CT image may provide a largest representation of the axial length(s) of the heart. As another example, one CT image may provide a largest representation of the axial length(s) or area of the left ventricle, whereas a separate CT image may provide a largest representation of the axial length(s) or area of the right ventricle.

In this regard, the subset of CT images identified by the AI module(s) may comprise any number of CT images (e.g., one or more), and the AI module(s) may obtain different largest measurements using different CT images of the subset of CT images (e.g., for providing heart measurement output).

In some embodiments, in addition, or as an alternative, to wall thickness, axial length and/or area measurements, the largest measurement(s) may include volume measurements. For instance, the subset of CT images identified by the AI module(s) (e.g., from CT image set input) may be selected to each include a representation of a heart, and a volume of the heart may be determined based on a combination of area or perimeter measurements of the respective portions of the heart represented in the CT images of the subset of CT images.

Thus, in some embodiments, the heart measurement output provided using the AI module(s) may comprise wall thickness, axial length, area, and/or volume measurements for one or more portions of the heart represented in the CT image set input (e.g., the set of CT images associated with the patient described hereinabove with reference to act 202). One will appreciate, in view of the present disclosure, that the heart measurement output may be associated with other heart structures not explicitly recited herein.

In some embodiments, the AI module(s) is/are configured to determine whether the CT image set input comprises a set of abdomen CT images or a set of chest CT images. For example, as noted above, a set of abdomen CT images may fail to capture all portions of a heart of a patient. Accordingly, in some embodiments, the heart measurement output obtained and/or provided by the AI module(s) is/are at least partially based on whether the CT image set input is a set of abdomen CT images or a set of chest CT images. For instance, in response to determining that CT image set input is a set of abdomen CT images, the AI module(s) may selectively refrain from attempting to compute volume measurements for the heart represented in the CT image set input (e.g., because such measurements would be incomplete in view of the set of abdomen CT images omitting one or more portions of the heart).

In accordance with act 204, the AI module(s) may be trained using one or more sets of training data. For example, a set of training data for training the AI module(s) to provide heart measurement output may include a plurality of training sets of CT images. Each training set of CT images of the plurality of training sets of CT images may be associated with a human patient. Furthermore, in some instances, for each training set of CT images of the plurality of training sets of CT images, the set of training data may include an identification or tagging of a respective subset of CT images. Each respective subset of CT images may include one or more respective CT images that provide a representation of a heart and/or a largest measurement of one or more portions of the heart (e.g., a heart as a single unit, a left ventricle, a right ventricle, a left atrium, a right atrium, a ventricular wall, etc.). The respective subsets of CT images may be manually identified by human users to provide a ground truth basis for configuring the AI module(s) to identify subsets of CT images based on CT image set input as described hereinabove. One will appreciate that the set of training data may comprise any control input or additional input to facilitate configuring the AI module(s) to subsequently identify subsets of CT images. One will also appreciate, in view of the present disclosure, that incorporating a variety of CT images with different acquisition parameters and/or from different institutions could improve the performance of the AI module.

Furthermore, for each training set of CT images of the plurality of training sets of CT images, the set of training data may include one or more respective heart measurements. The respective heart measurements may take on various forms and may be associated with various heart structures. For example, the respective heart measurements may comprise one or more wall thickness measurements, axial lengths, area measurements, volume measurements, or combinations thereof. The respective heart measurements may be associated with a heart as a single unit, a left ventricle, a right ventricle, a left atrium, a right atrium, a ventricular wall, and/or other structures. The respective heart measurements may be manually identified by human users (e.g., from the respective subsets of CT images) to provide a ground truth basis for configuring the AI module(s) to identify subsets of CT images based on CT image set input as described hereinabove. One will appreciate that the set of training data may comprise any control input or additional input to facilitate configuring the AI module(s) to subsequently provide heart measurements.

Act 206 of flow diagram 200 includes obtaining heart measurement output based on output of the AI module. The heart measurement output described hereinabove with reference to act 204 may provide a basis for determining whether a patient experiences cardiomegaly and/or a level of risk of cardiomegaly for the patient.

Accordingly, act 208 of flow diagram 200 includes, based on the heart measurement output, classifying the patient into one of a plurality of risk levels for cardiomegaly. As used herein, the term "risk" as it relates to cardiomegaly (e.g., "cardiomegaly risk," "risk levels for cardiomegaly," etc.) refers broadly to a likelihood that a patient is experiencing cardiomegaly and/or an estimated severity of cardiomegaly being experienced.

The plurality of risk levels for cardiomegaly referred to above may take on various forms. For example, in some embodiments, the plurality of risk levels may consist of a binary classification for indicating that a patient is either likely experiencing cardiomegaly (e.g., "1") or likely not experiencing cardiomegaly (e.g., "0"). In other embodiments, the plurality of risk levels provides a more granular indication of the likelihood that a patient is experiencing cardiomegaly. For instance, the plurality of risk levels may be represented as a plurality of qualitative levels (e.g., unlikely, slight likelihood, moderate likelihood, high likelihood) and/or a range of potential numerical values or scores that may indicate likelihood of cardiomegaly. In some implementations, the plurality of risk levels comprises a plurality of available percentile ranks for one or more heart measurements associated with a patient (e.g., a percentile ranking of heart measurements for a particular patient relative to heart measurements of other patients with a similar age, gender, inner chest size, outer chest size, etc.). The plurality of risk levels for cardiomegaly may also comprise multiple components, such as component for likelihood of experiencing cardiomegaly, a component for estimated severity of cardiomegaly being experienced, a component for expected degree of degradation over a time period, and/or others.

In some instances, act 208 includes classifying the patient into one of the plurality of risk levels for cardiomegaly based solely on the heart measurement output described above. However, the classification may additionally or alternatively depend on one or more other factors. In some embodiments, the classification is further based on one or more attributes of the patient associated with the heart for which the heart measurement output was generated. By way of example, a particular heart measurement associated with a large individual may not be indicative of cardiomegaly, whereas the same particular heart measurement associated with a small individual may be indicative of cardiomegaly. Thus, the classification of a patient into one of the plurality of risk levels for cardiomegaly may depend on patient attributes (e.g., percentile ranking as discussed above). Such attributes of the patient may include, for instance, body mass index (BMI), height, weight, girth, age, gender, race, inner chest size (e.g., a surrogate for lean body mass), outer chest size (e.g., a surrogate for fat body mass), and/or others.

The attributes of the patient may be obtained for classifying the patient's risk level for cardiomegaly in various ways and/or from various sources. For example, in some instances, the height and/or the girth of the patient may be estimated or obtained from the set of CT images for the patient. For instance, as noted above, an inner chest measurement associated with a particular patient may be indicative of the lean body mass for the patient, whereas an outer chest measurement associated with the patient may be indicative of the fat body mass for the patient. Furthermore, in some instances, the BMI, height, weight, girth, age, gender, race, CT field of view and/or other attributes may be obtained from user input stored in computer-readable memory in association with the patient. For example, a system may access stored electronic medical record (EMR) data that is associated with the patient and obtain one or more attributes of the patient therefrom. The EMR may contain information on whether or not the patient is actively being clinically managed or treated for cardiomegaly or an associated medical condition. The absence of clinical management or treatment for cardiomegaly or an associated medical condition may indicate a need for the patient to be triaged for appropriate care, either by the primary physician, the physician that ordered the CT exam, or a different caregiver that could include a nurse practitioner, physician assistant, internal medicine physician, family physician, cardiologist, a cardiac surgeon, and/or other medical practitioner.

Additionally, or alternatively, one or more attributes of the patient may be determined using an AI module based on the set of CT images for the patient. For example, an AI module may be trained to recognize the existence of a defibrillator or coronary calcification, which may affect the patient's classification of risk level for cardiomegaly.

The classification of the patient's risk level for cardiomegaly may be operable to trigger additional action associated with the patient, and the additional action may depend on the corresponding risk level for the patient. Act 210 of flow diagram 200 describes one such example action which may be implemented for at least some risk levels for cardiomegaly. In particular, act 210 of flow diagram 200 includes providing a notification to one or more relevant entities. A relevant entity may comprise, for example, the patient, a legal guardian of the patient, a primary care or other physician of the patient, and/or others. The notification may be configured to apprise the one or more relevant entities of the patient's risk of cardiomegaly, thereby enabling the patient to seek medical attention as appropriate for diagnosis and/or treatment of cardiomegaly and/or related conditions.

The notification provided to the relevant entity in accordance with act 210 may take on various forms and/or may be provided in various ways. For example, in some embodiments, the notification takes the form of a report generated for viewing by the one or more relevant entities. In some instances, the report includes one or more representation of the heart measurement output described hereinabove with reference to acts 204 and 206. Additionally, or alternatively, the report includes risk level into which the patient was classified according to act 208. The notification could additionally or alternatively be provided by telephone, email, facsimile, a clinical note in the EMR, a notification system through the EMR, and/or others.

Furthermore, in some instances, the report includes a representation of one or more CT images of the subset of CT images identified by the AI module as described hereinabove with reference to act 204. The representation of the one or more CT images may be labeled in a manner that emphasizes the heart measurement output. For example, one or more representations of the heart measurement output may be displayed over the one or more CT images, such as a highlighted segment showing area, one or more colored lines showing axial length, one or more colored lines showing wall thickness, etc. A report may comprise any additional or alternative graphics, charts, images, and/or information related to the patient not explicitly described herein.

In some embodiments, different types of reports may be generated for a patient depending on the risk level for cardiomegaly determined for the patient. For instance, for a low level of risk for cardiomegaly, a report may comprise less detail (e.g., by providing the classification associated with the patient and/or a list of symptoms to be aware of or other information related to cardiomegaly), whereas for a high level of risk for cardiomegaly, a report may comprise a high level of detail (e.g., by including one or more CT images with an overlay of heart measurement output).

In some instances, such as where a patient is classified as having a high risk of cardiomegaly, a report may comprise further action suggested for the patient (e.g., by providing contact information for a cardiologist or other medical practitioner or by providing a selectable link for initiating care with a medical practitioner).

In some instances, a report in accordance with act 210 is automatically generated and transmitted to the relevant entity, whereas, in other instances, the report is transmitted to an intermediate entity (e.g., a reviewing physician or other medical practitioner) for review before transmitting to the relevant entity. A report may be transmitted to the relevant entity through any suitable means, such as via e-mail, a printed document, text message, through a user-interactable interface (e.g., a patient portal), and/or other means.

In some instance, the reports from one or more patients may be entered into a digital patient tracking system. The patient tracking system could incorporate patient data from the output report as well as patient data from the EMR. The patient tracking system could provide a mechanism to follow up patient progress with referrals to clinical providers, including, for example, an ability to "snooze" a patient, putting their progress on hold temporarily but triggering follow up at a future time point.

Figure 8:
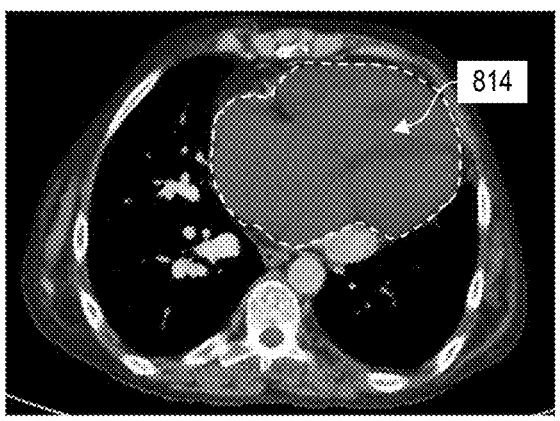
FIG. 8 illustrates example components of a report summarizing findings related to detection of cardiomegaly.
Figure 8:
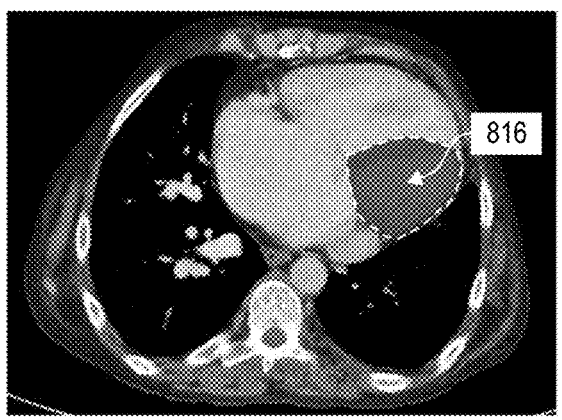
Figure 8:
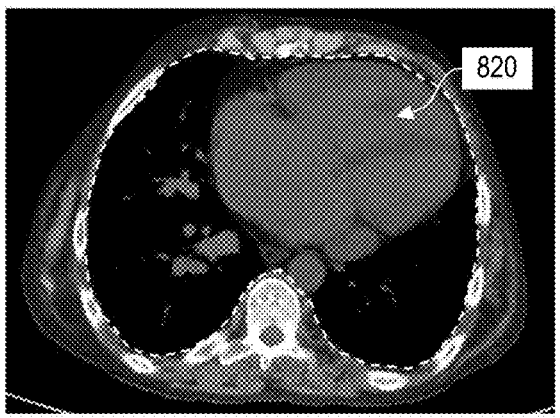
Figure 8:
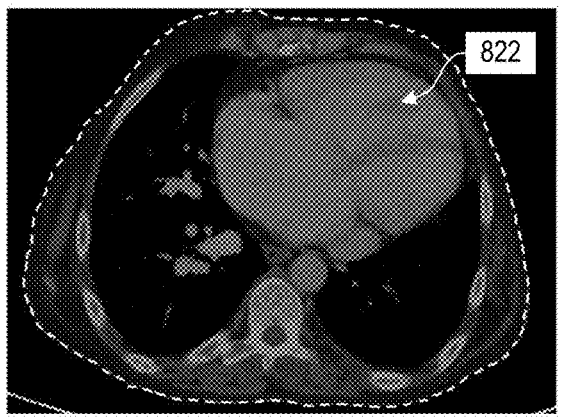

By way of illustration, FIG. 8 illustrates example components of a report 800 in accordance with act 210. For example, the report 800 includes patient information, such as the patient's name 802, medical record number 804, age 806, gender 808, type of imaging exam 810 ("CT abdomen and pelvis with contrast" in the example of FIG. 8), and/or clinical information 812 related to the patient and/or the CT imaging performed ("Status post fall" in the example of FIG. 8). In the example of FIG. 8, the report 800 depicts a whole heart area 814 and a left ventricle area 816. The report 800 also depicts heart measurements 818 associated with the whole heart area and the left ventricle area. The whole heart area 814, the left ventricle area 816, and/or the associated measurements 818 may be generated utilizing one or more AI modules, as discussed hereinabove with reference to acts 204 and 206.

The report 800 furthermore depicts an inner chest area 820 and an outer chest area 822, and measurements 824 associated with the same. The inner chest area 820, the outer chest area 822, and/or the associated measurements 824 may be generated utilizing one or more AI modules.

The report 800 furthermore includes a normal range 826 for whole heart measurements (84 to 120 square centimeters) and for left ventricle measurements (24 to 38 square centimeters). Expected or normal ranges for heart measurements may be associated with various patient attributes (e.g., age, gender, inner chest area (e.g., a proxy for lean body mass), outer chest area (e.g., a proxy for fat body mass), and/or others) based on collected heart measurements for sets of patients with such patient attributes. An appropriate expected or normal range for a particular patient (e.g., the patient for whom the report 800 is generated) may be selected based on one or more attributes of the patient, such as the age 806, gender 808, measurements 824 of inner chest area (e.g., a proxy for lean body mass) and/or outer chest area (e.g., a proxy for fat body mass), and/or others as discussed hereinabove. The normal range 826 shown in FIG. 8 may comprise a simplification of a more detailed distribution of expected heart measurements for a patient with particular attributes.

Based on one or more of the heart measurements 818 and/or one or more of the normal ranges 826, the patient may be classified with a risk level of cardiomegaly. In the illustrated example, the risk level is represented by percentile rankings (although other methods for representing risk of cardiomegaly are within the scope of the present disclosure, as discussed above). FIG. 8 illustrates a percentile ranking 828 based on a comparison of the patient's whole heart measurement to the normal range therefor. FIG. 8 also illustrates a percentile ranking 830 based on a comparison of the patient's left ventricle measurement to the normal range therefor. In the illustrated example, the percentile ranking 828 for the whole heart measurement of the patient is the $97^{th}$ percentile and is emphasized in the report with underlining to indicate that the patient is at risk for cardiomegaly or is experiencing cardiomegaly (other modes of emphasis are within the scope of the present disclosure). A user (e.g., the patient, a medical practitioner associated with the patient, etc.) may thus be prompted to take appropriate action based on the patient's apparent high risk for cardiomegaly (e.g., scheduling diagnostic treatment and/or testing).

In some implementations, illustrations, information, and/or components similar to those shown for the report of FIG. 8 may be utilized in a report in accordance with act 210. One will appreciate, in view of the present disclosure, that the specific organization, format, and/or content of the report 800 of FIG. 8 is provided by way of example only and is not limiting of the present disclosure. For example, a report 800 may omit the inner and/or outer chest area representations, and/or may include additional or alternative heart measurements, and/or may present risk for cardiomegaly in a different manner.

Providing a notification in accordance with act 210 may comprise other components separate from or in place of the report described hereinabove. In one example, a notification may comprise attempting or triggering an attempt to contact the relevant entity by phone or in-person to inform them of their risk of cardiomegaly (e.g., where the risk is classified as high).

In some embodiments of the present disclosure, a system refrains from providing a notification as described above with reference to act 210. For example, where a patient's risk for cardiomegaly is considered very low, a system may store heart measurement output for the patient in a database for longitudinal monitoring without providing a notification to a relevant entity. Should the risk be determined to be increased based on a subsequent set of CT images for the patient, a notification may be provided. In some embodiments, a system determines that a notification is unnecessary in view of patient attributes. For example, in some embodiments, a system may search medical record information (e.g., relevant current procedures terminology (CPT) codes and/or international statistical classification of disease and related health problems (ICD) codes) and determine that the patient is already being treated for cardiomegaly and/or related conditions, thereby removing the need to provide the relevant entity with a notification.

In some instances, patient attributes that may trigger a system to refrain from providing a notification may be determined from the set of CT images for the patient. For example, in some embodiments, an AI module is trained to recognize a defibrillator in a set of CT images. In response to detecting a defibrillator, a system may refrain from providing a notification (e.g., because the presence of the defibrillator indicates that the patient is aware and/or is being treated for issues related to cardiomegaly).

Accordingly, acts described in flow diagram 200 may facilitate opportunistic screening for cardiomegaly in an advantageous manner for individual patients. Flow diagram 300 provides acts associated with facilitating opportunistic screening for cardiomegaly for multiple patients. One or more acts of flow diagram 300 may be performed on a periodic basis using routine CT scans (e.g., for scans performed at a particular hospital, clinic, or other medical establishment) to reduce the number of patients unknowingly experiencing cardiomegaly.

In particular, act 302 of flow diagram 300 includes obtaining a CT imaging dataset, wherein the CT imaging dataset includes a plurality of sets of CT images, and wherein each set of CT images of the plurality of sets of CT images is associated with a respective patient of a plurality of patients. Each set of CT images of the plurality of sets of CT images of act 302 may be similar, in at least some respects, to the set of CT images described above with reference to act 202. For example, each set of CT images of the plurality of sets of CT images may comprise a routine set of CT images (e.g., a set of routine abdominal or chest CT images, or a set of whole body CT images).

Act 304 of flow diagram 300 includes determining a set of heart measurements comprising one or more separate heart measurements for each set of CT images of the plurality of sets of CT images. Each separate heart measurement of the set of heart measurements may be obtained using techniques similar to those described above with reference to act 204 of flow diagram 200. For example, the set of heart measurements may be determined using an artificial intelligence (AI) module configured to determine heart measurement output based on CT image set input (e.g., similar to FIGS. 5A through 5C).

Act 306 of flow diagram 300 includes, based on the set of heart measurements, classifying a subset of patients of the plurality of patients into one or more risk levels for cardiomegaly. The subset of patients may comprise any number of the plurality of patients (e.g., one patient, more than one patient, all patients, etc.). The risk levels for cardiomegaly of act 306 may be similar, in at least some respects, to the risk levels for cardiomegaly described hereinabove with reference to act 208 of flow diagram 200. For example, classifying the patients into the risk levels for cardiomegaly may be based on the respective heart measurements and/or respective patient attributes associated with each of the patients. In some instances, patient attributes may be obtained from the CT images, such as where an AI module measures inner chest and/or outer chest area, or recognizes a defibrillator or coronary calcification in CT images for a patient.

Act 308 of flow diagram 300 includes accessing medical record information associated with the subset of patients (e.g., the subset of patients classified into risk levels for cardiomegaly, in accordance with act 306). The medical record information may comprise EMRs for each patient and/or other stored medical data for each patient.

Act 310 of flow diagram 300 includes determining, based on the medical record information, one or more patients of the subset of patients that lack corresponding medical record information related to cardiomegaly. For example, a system may search through the EMRs and/or other data for each patient of the subset of patients for terms that would indicate that the patient has been diagnosed or is being treated for cardiomegaly and/or related conditions. For instance, a system may search through EMRs for relevant reference terms (e.g., for ICD and/or CPT codes) that may include: cardiologist; cardiomyopathy; cardiomegaly; myocardial infarction; ischemia; arrhythmia; defibrillator; pacemaker; cardiac catheterization; echocardiogram; cardiac gated CT; coronary artery disease; hypertensive heart disease; valvular heart disease; stenosis; regurgitation of the aortic, mitral, pulmonary or tricuspid valves; sub-acute bacterial endocarditis; congenital heart disorder; atrial septal defect; ventricular septal defect; patent ductus arteriosus; tetralogy of Fallot; Ebstein anomaly; coarctation of the aorta; pulmonary disease; primary pulmonary hypertension; COPD; pulmonary embolism; infectious myocarditis; infiltrative disease; deposition disease; amyloidosis; sarcoidosis; hypothyroidism; acromegaly; hemochromatosis; toxin-induced cardiomyopathy; autoimmune cardiomyopathy; eosinophilic myocarditis; idiopathic giant cell myocarditis; collagen vascular disease; atrial fibrillation; tachycardia-induced cardiomyopathy; arrhythmogenic right ventricular cardiomyopathy; idiopathic cardiomyopathy; abbreviations or initialisms thereof; combinations thereof; and/or other terms associated with cardiomegaly and/or related conditions.

In some embodiments, a system weighs medical record information related to cardiomegaly based on time. For example, an EMR for a patient may indicate that the patient has seen a cardiologist or received an echocardiogram within the last two years, which may cause the system to determine that the patient does not lack medical record information related to cardiomegaly in accordance with act 310. In another example, an EMR for a patient may indicate that the patient has seen a cardiologist or received an echocardiogram, but such events occurred more than two years in the past, which may cause the system to determine that the patient lacks medical information related to cardiomegaly in accordance with act 310.

Act 312 of flow diagram 300 includes providing a notification to one or more entities associated with the one or more patients. The notification and/or entities of act 312 may be similar, in at least some respects, to the notification and/or relevant entities described hereinabove with reference to act 210 of flow diagram 200 (e.g., see the report 800 of FIG. 6). Providing the notification may cause patients to seek or receive care to address latent cardiomegaly-related issues that might have otherwise been delayed or not received.

One or more acts of flow diagram 300 may be performed on a periodic basis using routine CT scans (e.g., for scans performed at a particular hospital, clinic, or other medical establishment) to reduce the number of patients unknowingly experiencing cardiomegaly. In some instances, a system may refrain from providing a notification, such as where a risk level associated with a patient is so high that it is unlikely that the patient is not already being treated or experiencing symptoms that would give rise to treatment. A system may also refrain from providing a notification to an entity associated with a particular patient in response to detecting a defibrillator within CT images for the particular patient.

Figure 4:
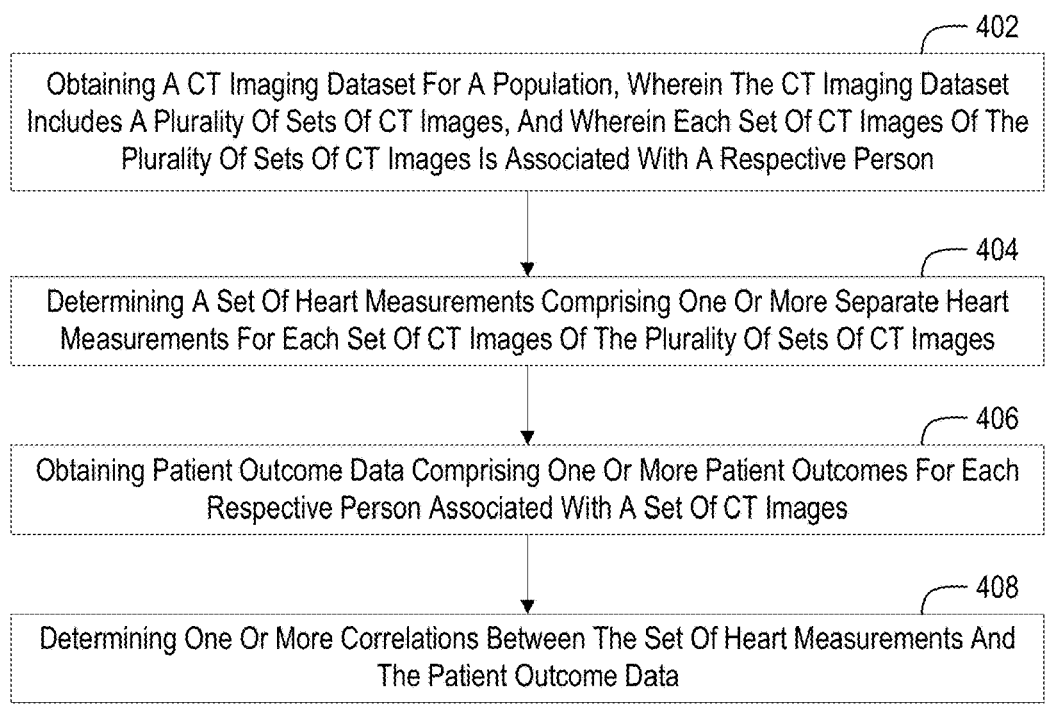
FIG. 4 illustrates an example flow diagram depicting acts associated with facilitating population health research using CT imaging datasets.

FIG. 4 illustrates an example flow diagram 400 depicting acts associated with facilitating population health research using CT imaging datasets. One or more acts of flow diagram 400 may be performed to explore relationships between heart measurements obtained from routine CT images and patient outcomes for different populations.

Act 402 of flow diagram 400 includes obtaining a CT imaging dataset for a population, wherein the CT imaging dataset includes a plurality of sets of CT images, and wherein each set of CT images of the plurality of sets of CT images is associated with a respective person. As referred to herein, a "population" refers to any set of two or more people. In some instances, a population may include a plurality of people that share a common attribute, such as race, gender, age, national origin, occupation, height, weight, BMI, and/or others. A population could include a plurality of people seen at one or more facilities or participating in a research study. In some instances, where a CT imaging dataset is captured for a population with one or more shared attributes, relationships between heart measurements, patient outcomes, and the shared attribute(s) may be determined.

Act 404 of flow diagram 400 includes determining a set of heart measurements comprising one or more separate heart measurements for each set of CT images of the plurality of sets of CT images. Determining a set of heart measurements in accordance with act 404 may follow techniques described hereinabove with reference to acts 204 of flow diagram 200 and 304 of flow diagram 300.

Act 406 of flow diagram 400 includes obtaining patient outcome data comprising one or more patient outcomes for each respective person associated with a set of CT images. Patient outcome data refers broadly to any stored information related to the medical status and/or progression of a patient over any number of timepoints. For example, a patient outcome data may relate to diagnostic data (e.g., diagnoses, measurement data, etc.), treatment data, disease progression data, death, other event(s), and/or a relative timing (e.g., relative to a treatment or other event) or patient age associated with any of the foregoing.

Act 408 includes determining one or more correlations between the set of heart measurements and the patient outcome data. Any suitable data processing and/or mathematical techniques may be used to determine correlations between the heart measurements and the patient outcome data. Such correlations may be used to establish and/or refine risk levels for cardiomegaly (e.g., discussed above with reference to acts 208 and 306) and thereby improve classification of patients into the risk levels based on heart measurements and/or other attributes of the patients. Such correlations may also provide important insights into the prevalence and/or progression of cardiomegaly for different populations of people.

Although the present disclosure focuses mainly on opportunistic screening for cardiomegaly, one will appreciate, in view of the present disclosure, that at least some of the principles described herein may be applied to facilitate opportunistic screening for other diseases.

Additional Details Related to Implementing the Disclosed Embodiments

The principles disclosed herein may be implemented in various formats. For example, the various techniques discussed herein may be performed as a method that includes various acts for achieving particular results or benefits. In some instances, the techniques discussed herein are represented in computer-executable instructions that may be stored on one or more hardware storage devices. The computer-executable instructions may be executable by one or more processors to carry out (or to configure a system to carry out) the disclosed techniques. In some embodiments, a system may be configured to send the computer-executable instructions to a remote device to configure the remote device for carrying out the disclosed techniques.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general purpose or special purpose computer system.

Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media (e.g., hardware storage devices) and transmission computer-readable media.

Physical computer-readable storage media includes hardware storage devices such as RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry program code in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Disclosed embodiments may comprise or utilize cloud computing. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, wearable devices, and the like. The invention may also be practiced in distributed system environments where multiple computer systems (e.g., local and remote systems), which are linked through a network (either by hardwired data links, wireless data links, or by a combination of hardwired and wireless data links), perform tasks. In a distributed system environment, program modules may be located in local and/or remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Application-specific Standard Products (ASSPs), System-on-a-chip systems (SOCs), Complex Programmable Logic Devices (CPLDs), central processing units (CPUs), graphics processing units (GPUs), and/or others.

As used herein, the terms "executable module," "executable component," "component," "module," or "engine" can refer to hardware processing units or to software objects, routines, or methods that may be executed on one or more computer systems. The different components, modules, engines, and services described herein may be implemented as objects or processors that execute on one or more computer systems (e.g., as separate threads).

CONCLUSION

Although the subject matter described herein is provided in language specific to structural features and/or methodological acts, it is to be understood that the subject matter defined in the appended claims is not necessarily limited to the described features or acts so described. Rather, the described features and acts are disclosed as example forms of implementing the claims.

Unless defined otherwise, all technical and scientific terms used herein have the same meaning as commonly understood by one of ordinary skill in the art to which the present disclosure pertains.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems and methods according to certain embodiments of the present disclosure may include, incorporate, or otherwise comprise properties or features (e.g., components, members, elements, parts, and/or portions) described in other embodiments. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment unless so stated. Rather, it will be appreciated that other embodiments can also include said features, members, elements, parts, and/or portions without necessarily departing from the scope of the present disclosure.

Moreover, unless a feature is described as requiring another feature in combination therewith, any feature herein may be combined with any other feature of a same or different embodiment disclosed herein. Furthermore, various well-known aspects of illustrative systems, methods, apparatus, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A computer-implemented method for facilitating opportunistic screening for cardiomegaly, comprising:
   obtaining a set of computed tomography (CT) images, the set of CT images capturing at least a portion of a heart of a patient, the set of CT images being captured for a purpose independent of assessing cardiomegaly, the set of CT images comprising CT images captured in a non-gated manner;
   using the set of CT images as an input to an artificial intelligence (AI) module configured to determine a heart measurement based on CT image set input by:
      identifying a subset of CT images from the CT image set input, the subset of CT images providing one or more largest measurements associated with a heart represented in the CT image set input, and
      providing heart measurement output based on the one or more largest measurements associated with the heart represented in the CT image set input, wherein the AI module is trained using training data comprising (i) a plurality of training sets of CT images and (ii) for each training set of CT images of the plurality of training sets of CT images, an identification of a respective subset of CT images and a respective heart measurement based on the respective subset of CT images;
   obtaining heart measurement output based on output of the AI module; and
   based on the heart measurement output, classifying the patient into one of a plurality of risk levels for cardiomegaly, the classification being operable to trigger additional action based on the corresponding risk level for cardiomegaly.

2. The computer-implemented method of claim 1, wherein the set of CT images comprises a set of abdominal CT images.

3. The computer-implemented method of claim 1, wherein the set of CT images comprises a set of chest CT images.

4. The computer-implemented method of claim 1, wherein the AI module comprises a machine learning module.

5. The computer-implemented method of claim 4, wherein the one or more largest measurements associated with the heart represented in the CT image set input comprises a ventricular wall thickness and/or an axial length and/or area of one or more of: the heart represented in the CT image set input, a right ventricle thereof, a left ventricle thereof, a right atrium thereof, and/or a left atrium thereof.

6. The computer-implemented method of claim 1, wherein the AI module comprises a machine learning module configured to:
   identify a subset of CT images from the CT image set input, each CT image of the subset of CT images providing a representation of a heart represented in the CT image set input; and
   provide heart measurement output comprising a volume measure of the heart represented in the CT image set input, the volume measure being determined using the subset of CT images.

7. The computer-implemented method of claim 4, wherein:
   the machine learning module is further configured to determine whether the CT image set input comprises a set of abdomen CT images or a set of chest CT images, and
   the heart measurement output is at least partially based on whether the CT image set input comprises a set of abdomen CT images or a set of chest CT images.

8. The computer-implemented method of claim 1, wherein classifying the patient into one of the plurality of risk levels for cardiomegaly is further based on one or more patient attributes of the patient.

9. The computer-implemented method of claim 8, wherein the one or more patient attributes comprise one or more of: body mass index (BMI), body surface area, inner chest size, outer chest size, height, weight, girth, age, gender, race, and/or field of view of the axial CT image.

10. The computer-implemented method of claim 1, wherein, for at least one of the plurality of risk levels for cardiomegaly, the additional action comprises providing a notification to one or more relevant entities.

11. The computer-implemented method of claim 10, wherein the one or more relevant entities comprises the patient or a physician for the patient.

12. The computer-implemented method of claim 10, wherein providing the notification to the one or more relevant entities comprises generating a report and providing the report to the one or more relevant entities.

13. The computer-implemented method of claim 12, wherein the report comprises the heart measurement output and/or one or more subsets of CT images of the set of CT images.

14. The computer-implemented method of claim 13, wherein the report comprises a percentile ranking associated with the heart measurement output relative to heart measurements of other patients.

15. The computer-implemented method of claim 1, wherein the heart measurement output comprises a major axis of at least part of the heart of the patient.

16. A system for facilitating opportunistic screening for cardiomegaly, the system comprising:
   one or more processors; and
   one or more hardware storage devices that store instructions that are executable by the one or more processors to configure the system to:
      access a set of computed tomography (CT) images, the set of CT images capturing at least a portion of a heart of a patient, the set of CT images being captured for a purpose independent of assessing cardiomegaly, the set of CT images comprising CT images captured in a non-gated manner;

process the set of CT images using an artificial intelligence (AI) module configured to determine a heart measurement based on CT image set input by causing the AI module to:
  identify a subset of CT images from the CT image set input, the subset of CT images providing one or more largest measurements associated with a heart represented in the CT image set input, and
  provide heart measurement output based on the one or more largest measurements associated with the heart represented in the CT image set input, wherein the AI module is trained using training data comprising (i) a plurality of training sets of CT images and (ii) for each training set of CT images of the plurality of training sets of CT images, an identification of a respective subset of CT images and a respective heart measurement based on the respective subset of CT images; and
based on the heart measurement output, classify the patient into one of a plurality of risk levels for cardiomegaly, the classification being operable to trigger additional action based on the corresponding risk level for cardiomegaly.

* * * * *